United States Patent [19]
Nakade

[11] Patent Number: 5,154,893
[45] Date of Patent: Oct. 13, 1992

[54] AIR CIRCULATOR

[75] Inventor: Kouichi Nakade, Tokyo, Japan

[73] Assignee: Masuda Harmo K.K., Tokyo, Japan

[21] Appl. No.: 625,673

[22] Filed: Dec. 13, 1990

[30] Foreign Application Priority Data

Dec. 15, 1989 [JP] Japan .................................. 1-325570
Nov. 27, 1990 [JP] Japan .................................. 2-324734

[51] Int. Cl.⁵ .............................................. A62B 11/00
[52] U.S. Cl. ........................................ 422/124; 422/4;
422/5; 422/122; 422/306; 55/279; 55/387;
55/471; 55/473
[58] Field of Search .................. 422/124, 306, 4, 5,
422/122; 55/279, 471, 472, 473, 387

[56] References Cited
U.S. PATENT DOCUMENTS

| 4,346,059 | 8/1982 | Spector | 422/306 |
| 4,526,592 | 7/1985 | Armbruster | 55/472 |
| 4,541,847 | 9/1985 | Oie et al. | 55/279 |
| 4,553,992 | 11/1985 | Boissinot et al. | 55/279 |

Primary Examiner—Robert J. Warden
Assistant Examiner—Laura E. Collins
Attorney, Agent, or Firm—Kanesaka and Takeuchi

[57] ABSTRACT

An air circulator comprises an inlet open to an interior space, an outlet open to the interior space, an air path connecting the inlet with the outlet, and a blower interfering with the air path and driven by motor. A container is provided to connect with the air path and includes therein air treatment agents such as deodorants and aromatics. Furthermore, a venturi tube is provided facing the outlet to suck and discharge the surrounding air together with the air ejected from the outlet, while treating the air in the interior space.

19 Claims, 13 Drawing Sheets

AIR CIRCULATOR

BACKGROUND OF THE INVENTION

1. Field of the Invention

This invention relates to a device to circulate the air in the interior of a building such as a hospital, a beauty parlor, a hotel and restaurant, or of a traffic means such as an automobile, a railway car, an aircraft and a ship, and more particularly, to an air circulator to circulate the air while giving out fragrance or ozone, and removing odor and dust.

2. Description of the Prior Art

Generally, commercially available conventional air circulator is used to circulate the air in an interior space to enhance the efficiency of air conditioning therein.

Recently, it is desired to produce a comfortable indoor atmosphere in a vehicle, a beauty parlor, a barrom as well as a hospital, by absorbing smell common to such facilities. In a hotel or an aircraft, on the other hand, it is expected that aroma unique to the hotel or aircraft is diffused to eliminate for differentiation by odor.

With such conventional air circulators, however, it is intended only to stir the air in the interior. They are not able to absorb any smell and diffuse any fragrance. They can not remove dust, either.

It may be possible to provide an air circulator of the prior art with deodorant or aromatic in its air inlet or outlet. In such an air circulator, however, all the air circulating in the interior is subjected to the deodorant or aromatic and to increase air circulation resistance greatly, while deteriorating air stirring efficiency. In addition, this necessitates to install a blower of a larger capacity and a more powerful motor to drive the blower. What is worse is that air causes noise when it passes the deodorant or aromatic, spoiling the quiet atmosphere. The deodorant or aromatic may lose its effect sooner.

In a hotel or a similar facility, on the other hand, it may be planned to give out fragrance indoors via its every air conditioning system. If this is the case, the whole air conditioning system inevitably will need an installation of a large scale to this purpose, but it will be impossible to carefully satisfy the particular conditions of its rooms, lobbies, and restaurants in terms of odor because they are under different circumstances.

SUMMARY OF THE INVENTION

It is therefore an object of the present invention to provide an air circulator simple in construction and capable of circulating air and diffusing odor.

It is another object of the present invention to provide an air circulator which is able to remove smell and dust, thereby solving the above problems.

It is another object of the present invention to provide a cassette which can be removably attached and facilitate renewal of an air treatment agent and a filter.

The present invention proposed in view of the above is an air circulator provided with an inlet open to an interior space, an outlet open thereto, an air path connecting the inlet with the outlet, a blower interfering with the path, a motor to drive the blower, wherein the improvement comprises a container arranged to intervene in the path and to contain any of air treatment agents such as deodorant and aromatic, and a venturi tube arranged to face the outlet to suck the surrounding air and discharge it together with the air ejected from the outlet.

According to another feature of the present invention, the air circulator is equipped in the path with a filter parallel to the container so as to filter the air in the interior.

According to another feature of the present invention, a container is integrated with a filter in a cassette, which can be attached removably to the inlet.

Such an air circulator thus composed according to the present invention is mounted onto the ceiling of an indoor space or nearby. If such an indoor space is in a hospital which generates smell common thereto, the container is equipped with deodorant. When a drive motor rotates, with air in the interior space passes through the inlet and the air path before it is absorbed in the blower while being subject to the deodorant in the container. The deodorized air is discharged from the outlet to the venturi tube, which absorbs the surrounding air around the inlet and discharges it together with the air coming from the outlet. The air in the interior space is thereby stirred in an efficient manner.

If such an air circulator according to the present invention is used in a hotel room, the container is provided with any aromatic unique to the hotel so that the air in the room may be stirred and diffused with its own odor, using the blower as mentioned above.

It is also possible to install a filter parallel to the container so as to clean the air in the room in addition to circulating and deodorizing or giving out fragrance to the air.

One feature of the present invention enables the air circulator to renew the cassette with ease when any air treating agent such as deodorant and aromatic has lost its effect or the filter has caused clogging.

DETAILED DESCRIPTION OF THE PREFERRED EMBODIMENTS

The subject matter of the present invention will become manifest to those versed in the art upon making reference to the detailed description of the embodiments which follow and the accompanying sheets of drawings.

Figure 1:
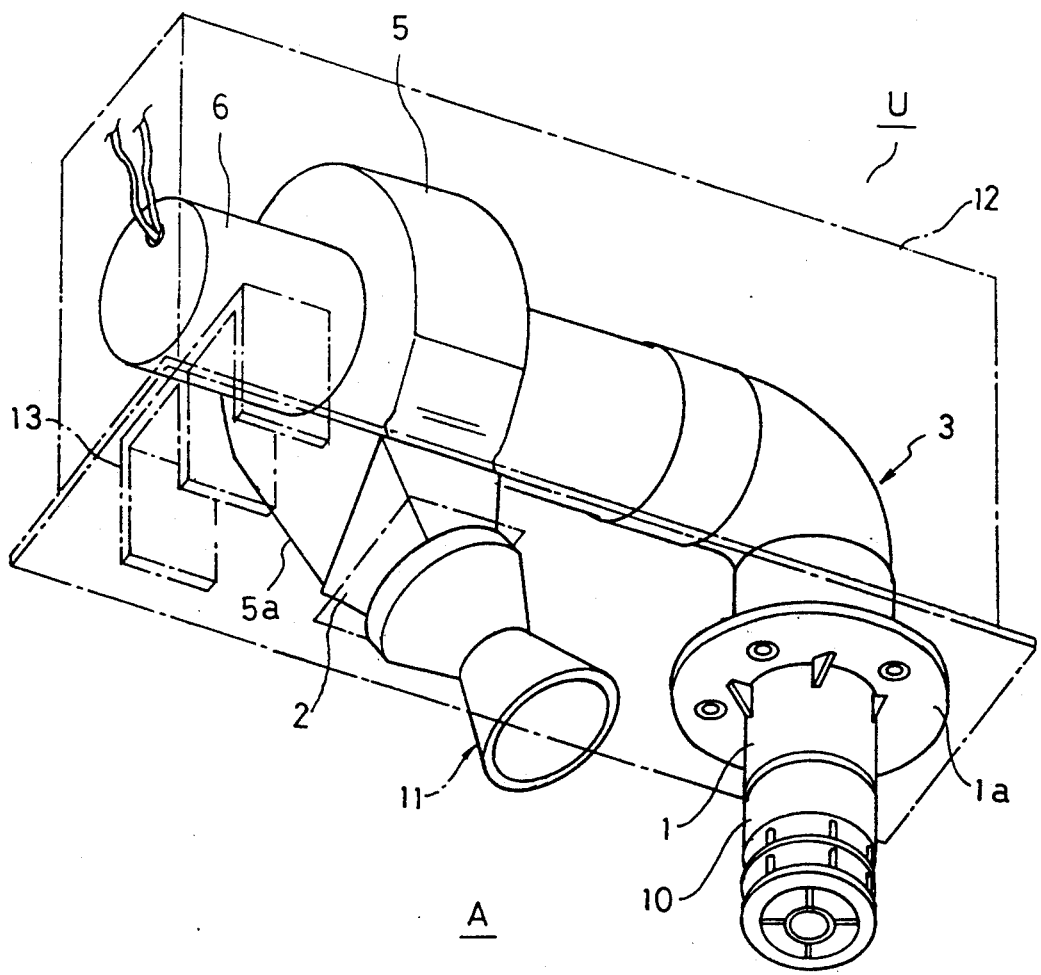
FIG. 1 shows a perspective view of an air circulator of an embodiment according to the present invention.
Figure 2:
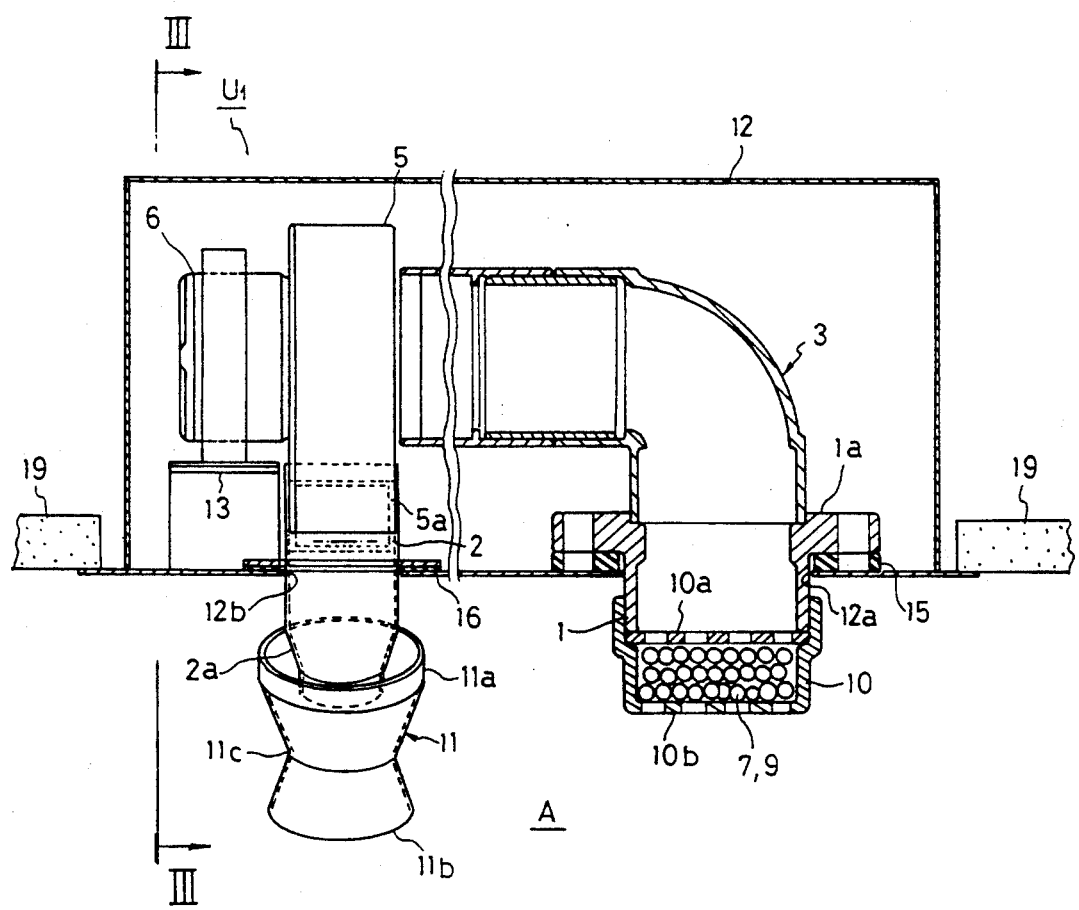
FIG. 2 is a side sectional view thereof.
Figure 3:
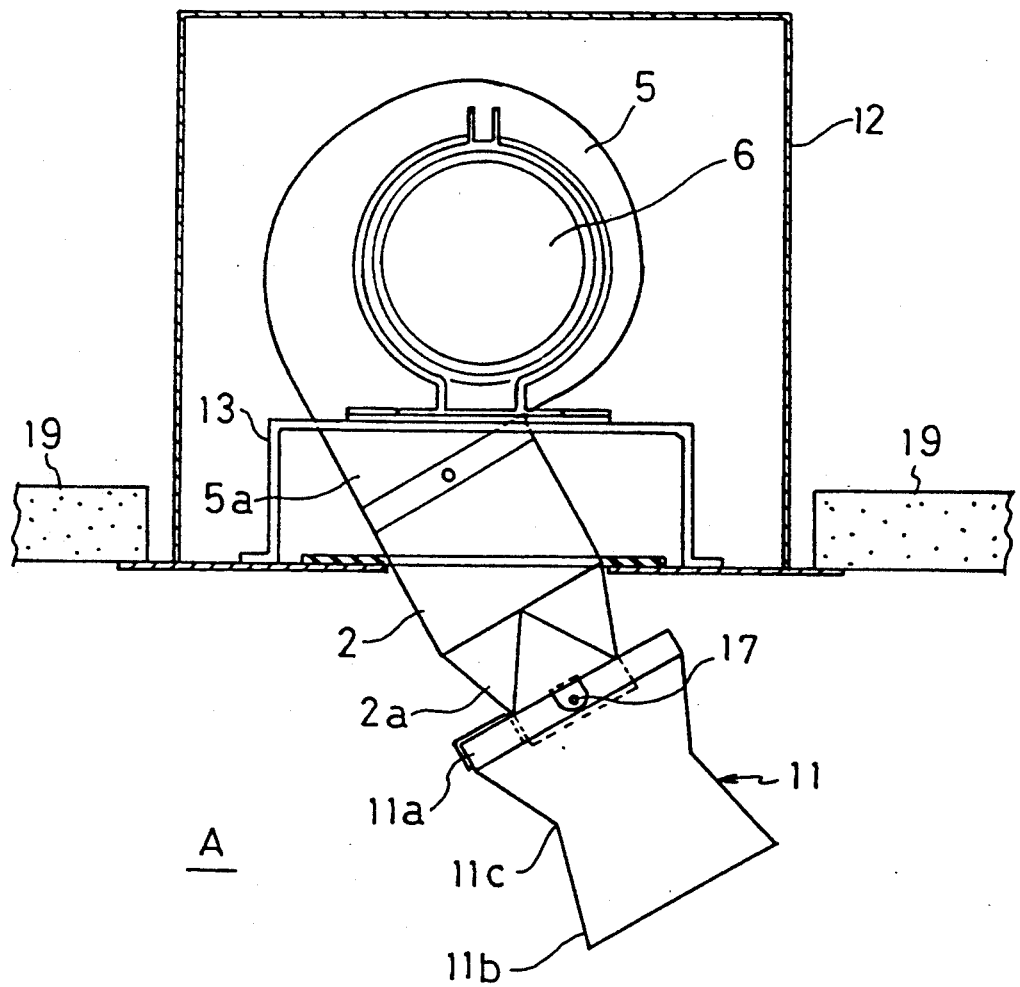
FIG. 3 is a sectional view taken along line III—III of FIG. 2.

As shown in FIG. 1 through FIG. 3, an air circulator U has a case 12, where two openings 12a and 12b are formed at the bottom. A bracket 13 is also secured to the case 12. There are provided in the case 12 a block of duct 3 as an air path, a silocco fan blower 5 and an electric motor 6 to drive the same. An inlet 1 of the duct 3 projects outward from the opening 12a and is secured to the case 12 with a flange 1a by way of a packing 15. The motor 6 is secured to the bracket 13.

A container member 10 is attached removably to the tip projecting outward of the inlet 1, and the container member 10 is constructed to have meshes at the top 10a and the bottom 10b not to prevent the air from flowing, and is equipped with an deoderant 7 or an aromatic 9 as adequate.

An inlet 2 is secured to the discharge port 5a surrounded by the silocco fan blower cover, and the outlet 2 projects outward from the opening 12b of the case 12 while the opening 12b is closed with a packing 16. The case 12 connected to the discharge port 5a is rectangular in section, but has an approximately circular discharge nozzle 2a. A venturi tube 11 is fitted to the front end of the nozzle 12a to be able to adjust an angle thereof by a fixture 17. The venturi tube 11 is composed of a large-diameter inlet portion 11a, a middle drawn section 11c and a large-diameter outlet portion 11b. The surrounding air sucked together with the air discharged from the nozzle 2a reaches the portion 11a and is discharged through the portion 11b, together with the air coming from the nozzle 2a.

Figure 4:
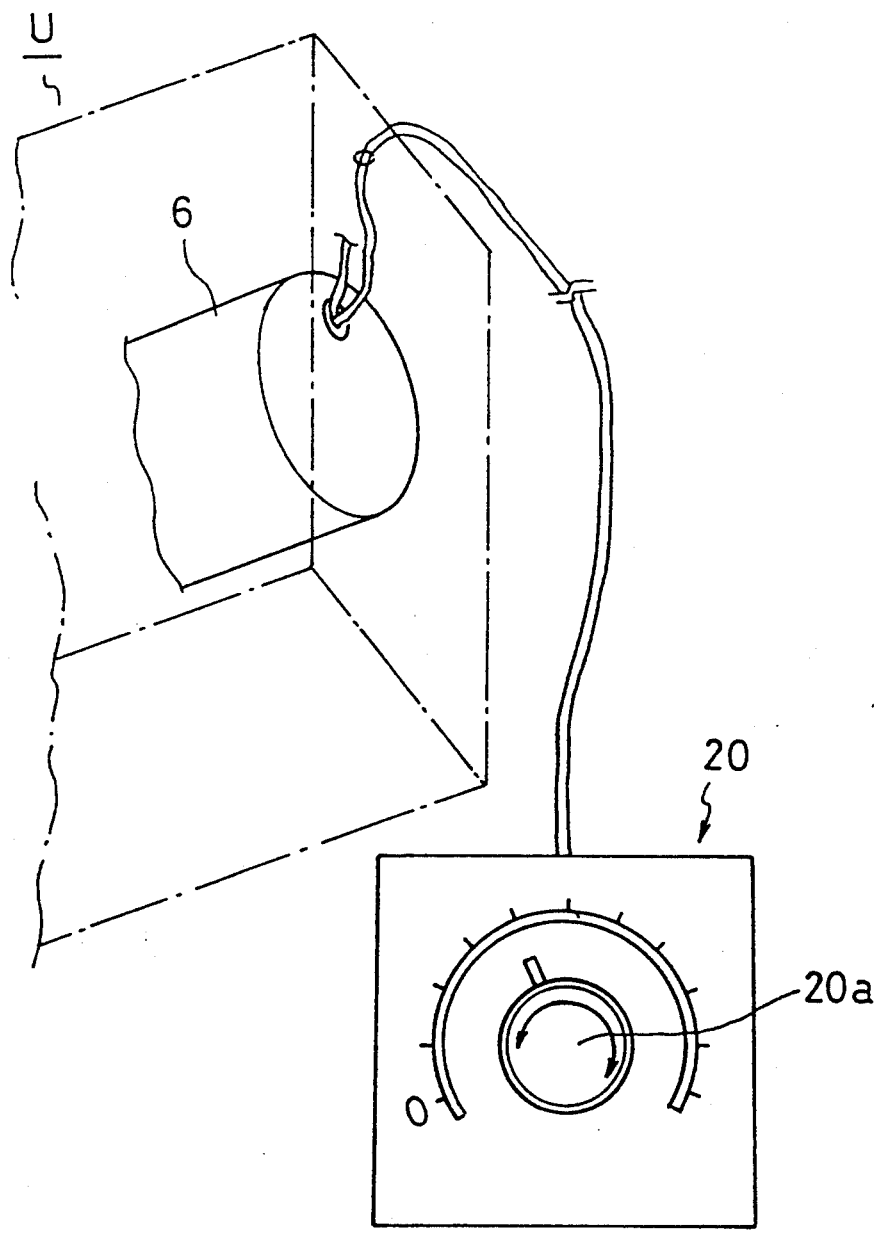
FIG. 4 is an elevation view of a controller of the embodiment.

There is installed, on the other hand, a controller 20 on a given wall of an indoor space A as shown in FIG. 4. The controller 20 is equipped with a knob 20a, and wired to the motor 6. With the knob 20a, the motor 6 and consequently, the silocco fan blower 5, can be adjusted for rotation.

The air circulator U thus composes is embedded in the ceiling 19 of the interior space A, and the container member 10, the nozzle 2a and the venturi tube 11 are arranged to project downward from the ceiling 19. If the space A has such a smell as common to a hospital, a beauty parlor and a vehicle, the container member 10 with the deodorant 7 in is mounted onto the inlet 1. When the motor 6 is then put into operation by adjusting the knob 20a of the controller 20, the silocco fan blower 5 starts rotating at a given speed so that the air in the interior space A is absorbed into the duct 3, passing the deodorant 7 in the container 10. The air is deodorized while the deodorant 7 diffuses deodorant ingredients. As a result, the deodorized air is blown out by means of the blower 5 from the nozzle 2a, together with the deodorant containing air. The air discharged from the nozzle 2a to the venturi tube 11 invloves the air in the surrounding of the large-diameter inlet portion 11a of the venturi tube 11, and they are ejected downward through the large-diameter output portion 11b. If the interior space A is heated, the hot air in the vicinity of the ceiling is sucked by the venturi 11 for helping the air coming from the nozzle 2 to provide a better air circulation efficiency and to serve to maintain the interior temperature constant.

If an air circulator $U_1$ embodied according to the present invention is installed in a room A of a hotel, a container 10 is furnished with an aromatic 9 unique to the hotel. The air in the foom A is subjected to the aromatic 9 and scented while blown by a blower 5. The air is then sent out through a nozzle 2a to the interior space, together with the air sucked by the venturi tube 11.

Figure 5:
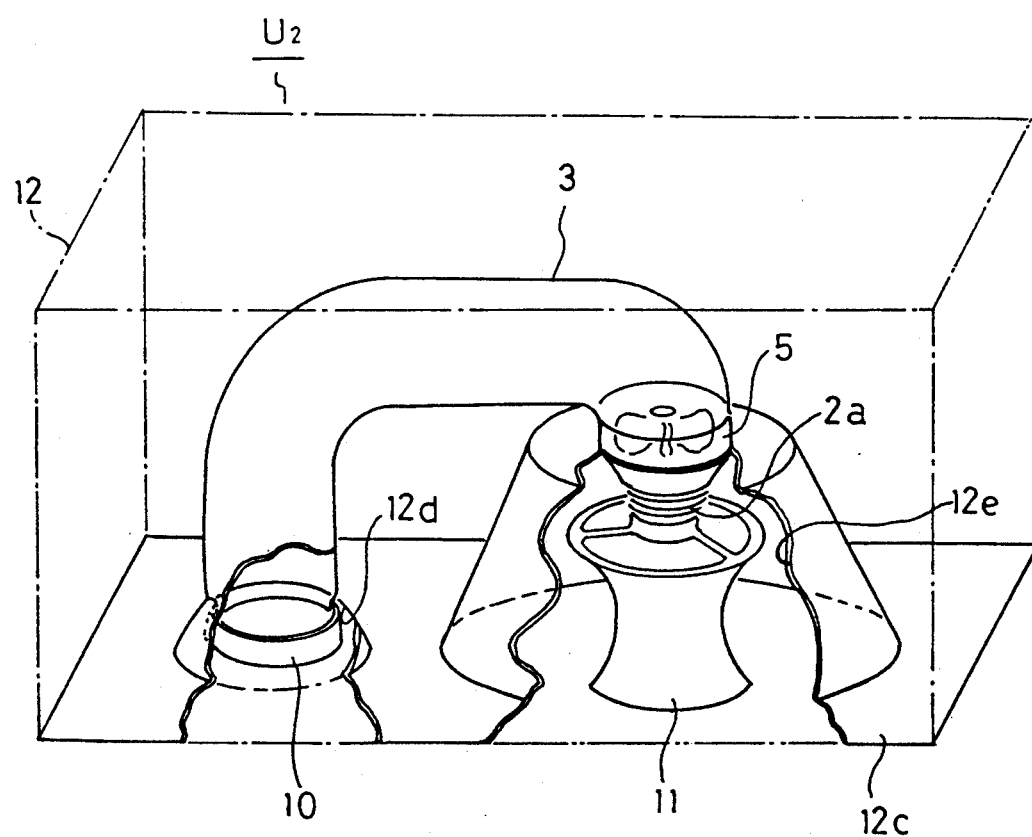
FIG. 5 through FIG. 7 show perspective views, partially broken, of different embodiments according to the present invention.
Figure 6:
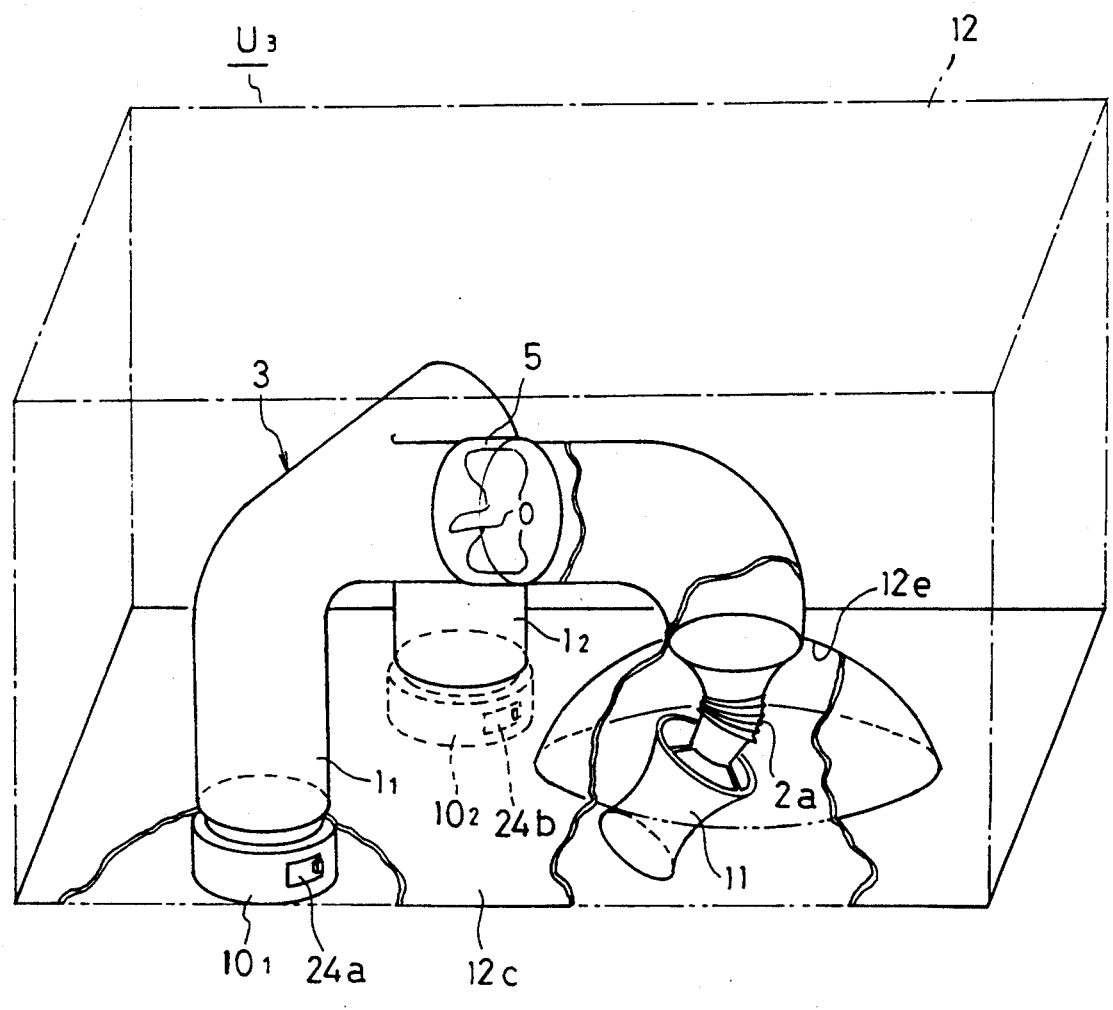
Figure 7:
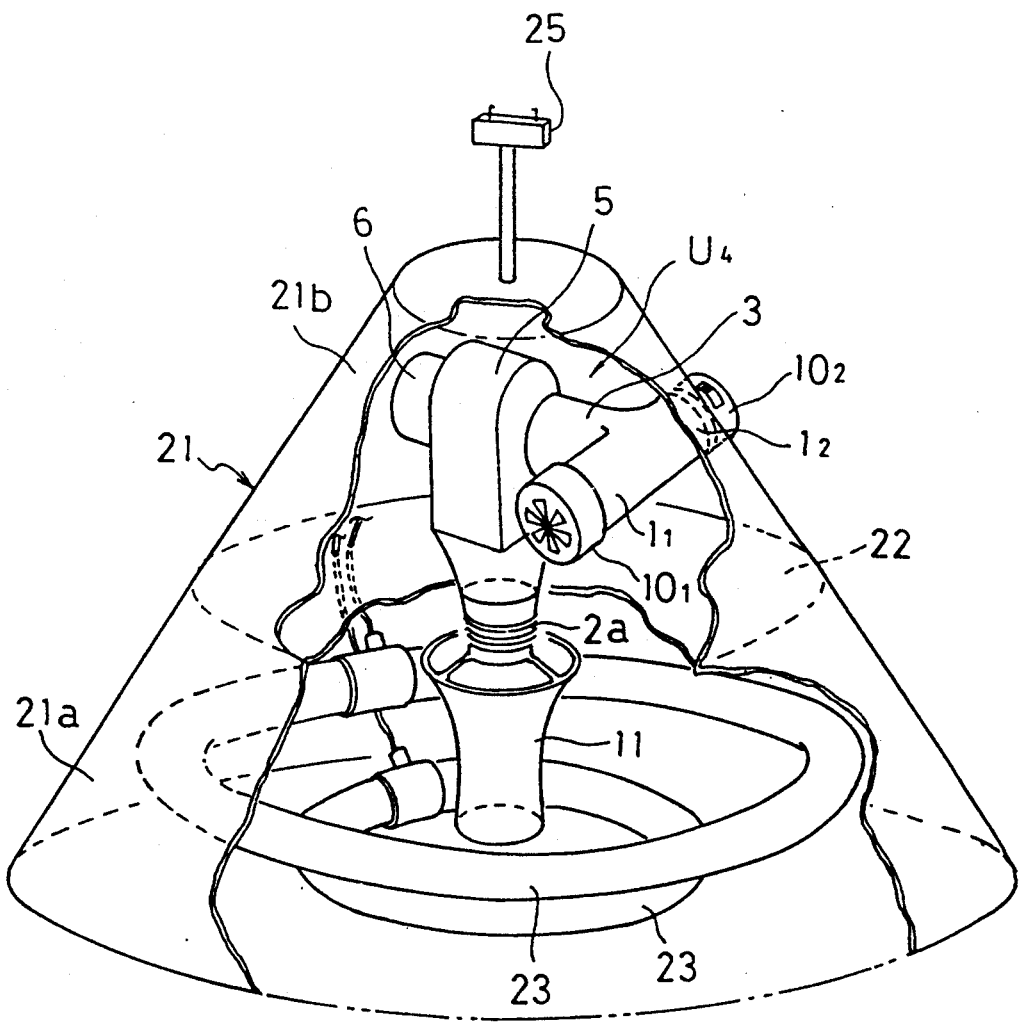

Referring now to FIG. 5 through 7, partially modified embodiments according to the present invention will be described.

As shown in FIG. 5, an air circulator $U_2$ comprises an axial-flow fan 5 as a blower, and a container member 10 and a venturi tube 11 are respectively housed in concavities 12d and 12e formed in the bottom plate 12c of a case 12. In addition, a nozzle 2a is formed of a bellows member and is connected at the front end with the venturi tube 11.

The air circulator $U_2$ is, accordingly, such that the air absorbed after passing any deodorant or any aromatic in the container member 10 is sent out to the venturi tube 11 by way of the nozzle 2a, and ejected downward together with the air in the concavity 12e, sucked by the venturi tube 11. The direction of the air coming from the venturi tube 11 can be then adjusted by orienting the bellows nozzle 2a differently.

Such an embodiment of the present invention costs less and can maintain well the interior of a hotel room or a beauty parlor beautiful because the axial-flow fan 5 is cheaper and no venturi tube projects downward from the ceiling.

An air circulator $U_3$ as shown in FIG. 6 is also provided with an axial-flow fan 5 and a nozzle 2a made of a bellows member. In additon, a venturi tube 11 is housed in a concavity 12e formed in the bottom plate 12c of a case 12. Furthermore, in such an air circulator, a duct 3 is equipped with forked inlets $1_1$, $1_2$, each of which is provided at the front end a container member $10_1$, $10_2$. The container members $10_1$, $10_2$ have shutters 24a, 24b respectively. In addition to this, the container member $10_1$ accommodates a deodorant while the container member $10_2$ has an aromatic.

The air circulator $U_3$ thus composed is, accordingly, able to open the shutter 24a and close the shutter 24b so that the air sucked by the axial-flow fan 5 flows only in the container member $10_1$ with a deodorant in for the purpose of air deodorizing and circulating. It also works to open the shutter 24b and close the shutter 24a as well so that the air is sucked by the axial-flow fan only through an aromatic to emit fragrance while it is circulated in the interior.

In addition, if the shutter 24a and 24b are opened, part of the air sucked by means of the axial-flow fan 5 is subjected to the deodorant and the rest is to the aromatic, removing thereby smell from the air and giving out a unique fragrance thereto in the interior.

The air circulator $U_3$ embodied according to the present invention enables air deodorizing or fagrance emission or both at the same time when so necessary.

An air circulator $U_4$ as shown in FIG. 7 is attached within a circular fluorescent lamp shade. The shade 21 is almost conic, and it is divided in the middle by means of a partition 22, under which there is provided a lower chamber 21a supporting circular fluorescent lamps 23, 23. There is provided the air circulator $U_4$ in an upper chamber 21b. The air circulator $U_4$ comprises a blower fan 5, an electric motor 6 and a duct 3 with inlets $1_1$, $1_2$ extendible horizontally. There are provided container members $10_1$, $10_2$ respectively at the front ends of the inlets $1_1$, $1_2$ projecting from the side of the shade 21 while a bellows nozzle 2a projects downward from the blower fan 5 to the partition 22. In addition, there is provided a venturi tube 11 connecting to the nozzle 2a and projecting to the center of the circular fluorescent lamps 23.

The air circulator $U_4$ as described above is installed when the fluorescent lamp shade 21 is mounted onto the ceiling by using a fixture 25. When the fluorescent lamps 23 are switched on, an electric motor 6 is automatically put into operation to deodorize or give out a unique fragrance to and circulate the air in the interior as the embodiment in FIG. 6. In case the electric motor 6 is interlocked with the fluorescent lamps 23 whenever the lamps are switched on and off, the air circulator $U_4$ is turned on and off at the same time, preventing it from being left unswitched off. Besides this, the air circulator may be to the controlled by a special controller (as described in FIG. 4). According to the present embodiment, the air circulator $U_4$ is also so designed as to be installed within the shade 22, eliminating thereby any ceiling or interior work and any difficulty in installing indoors. The air circulator has a deodorant or an aroma in the container member 10, but an ozone generator or a similar thing can also be contained instead. Furthermore, the casing 12 of the air circulator $U_4$ is attached inside the ceiling, but it also can be attached under the ceiling or on a top of a wall or exposed to the interior.

Figure 8:
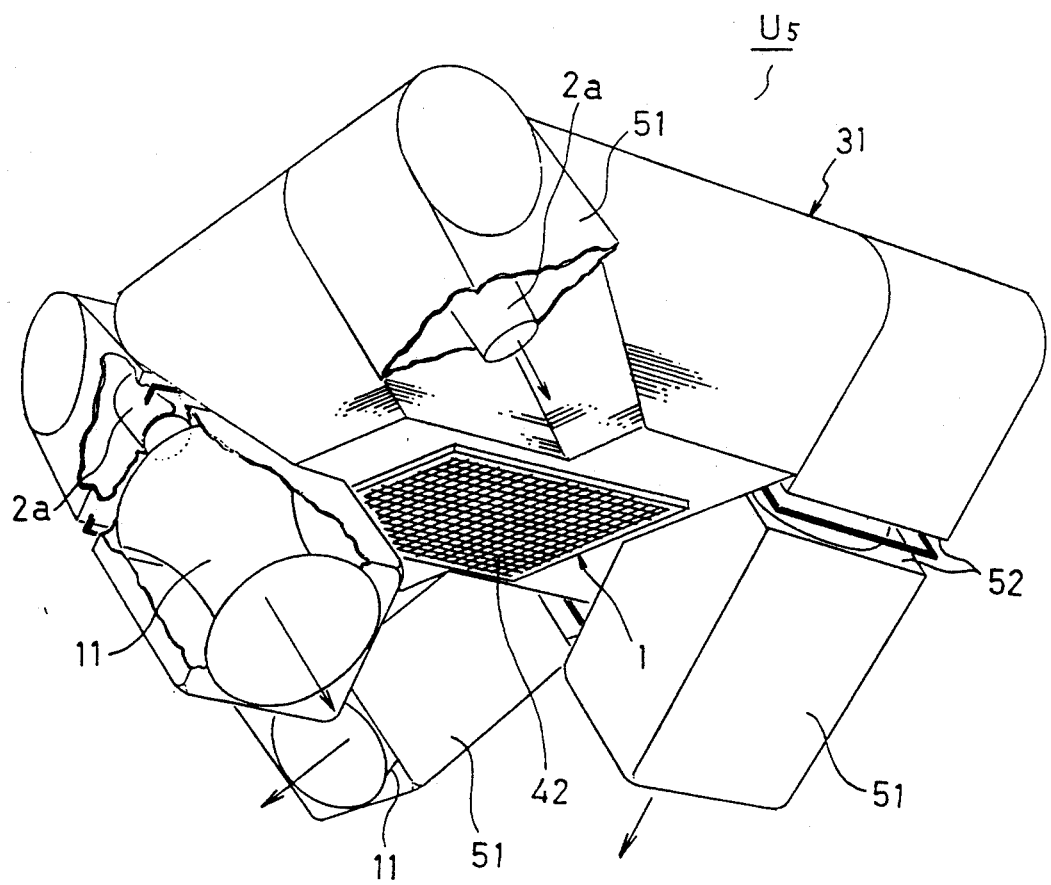
FIG. 8 is a perspective view of another embodiment of the present invention.
Figure 9:
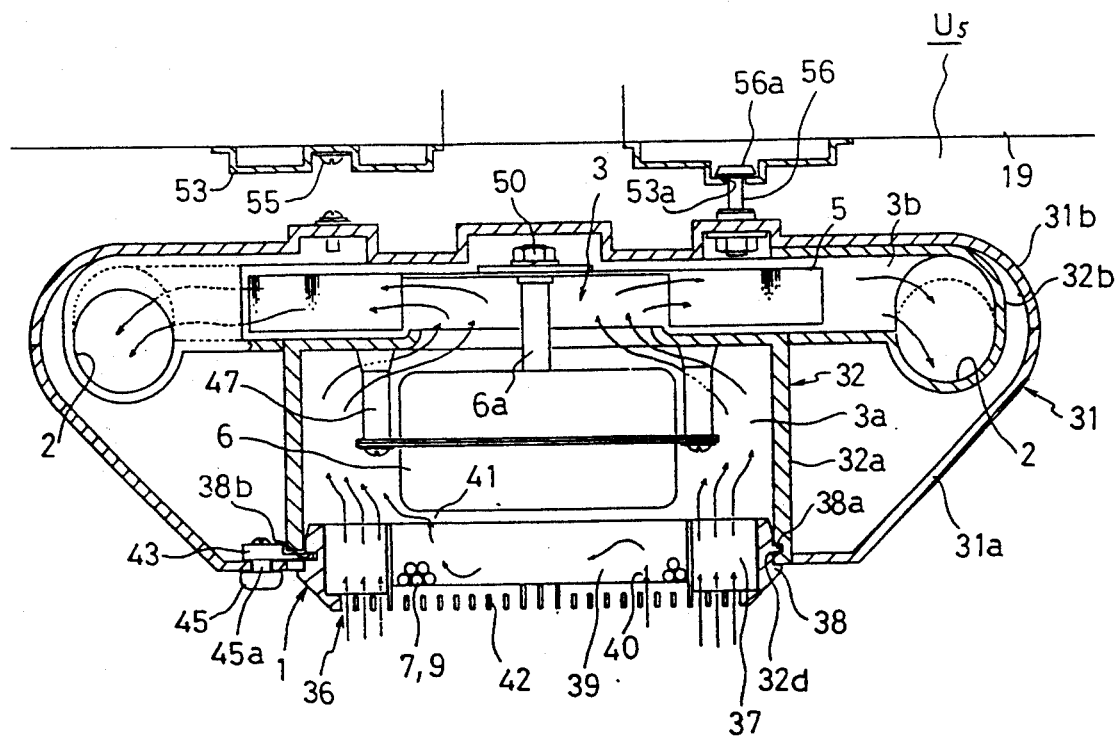
FIG. 9 is a longitudial evelvation view thereof.
Figure 10:
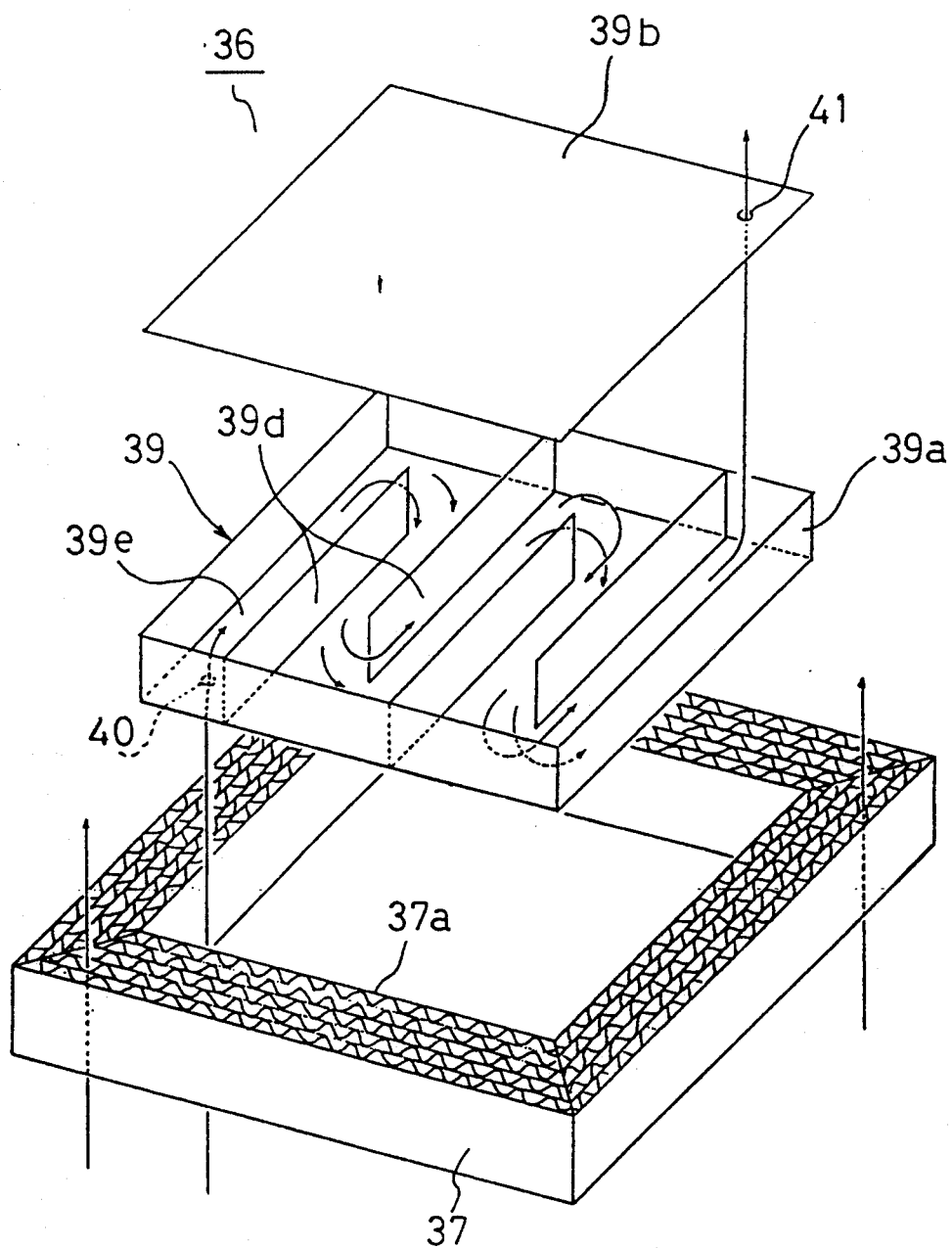
FIG. 10 is an exploded perspective view of the cartridge (container) of the embodiment.

Referring now to FIG. 8 through FIG. 10, other embodiments according to the present invention will be described.

An air circulator $U_5$ has a body 31 comprising a first case 31a and a second case 31b connected thereto. In the body 31, there is secured a duct 32 comprising a first duct 32a and a second duct 32b integrated therewith. The duct 32 constitutes an air path 3 composed of a first air path 3a in the first duct 32 and a second air path 3b in the second duct 32b, the paths being connected with each other.

There is a cassette 36 removably attached to the inlet 1 constituted by the opening of the first duct 32a, and the cassette 36 is composed of an air filter 37 having a hole 37a in the center thereof and a cartridge (container) 39 fitted in the hole 37a as shown in FIG. 10 in detail. The cartridge 39 is composed of a cartridge body 39a, a lid 39b and a plurality of partitions 39d to divide the cartridge body 39a into a plurality of chambers connected with each other.

At a corner of the bottom plate 39e of the cartridge body 39a or at an end of a chamber, there is perforated a vent hole 40, and at a corner of the lid 39b corresponding to the other edge of the chamber, there is perforated a vent hole 41 to discharge air. The cartridge thus composed has a long air path. A deodorant 7 or an aromatic 9 as an air treatment agent is contained in the cartridge 39.

The cassette 36 is installed removably to a frame member 38 having a mesh panel 42 at the bottom. A projection 38a which is a part of the frame member 38 is fitted in a concavity 32d of the first duct 32a, and a concavity 38b on another side of the frame member 38 is engaged with a free end of an engaging member 43, so that the cassette 36 is supported by the body 31. The engaging member 43 is secured to the axis 45a of a knob 45 rotably fitted to the front of the first case 31a, and passes through a hole of the first duct 32a. When the knob 45 is turned to disengage the engaging member 43 from the concavity 38b, the cassette 36 can be removed from the inlet 1 of the body 31.

Inside the duct 32a, there is secured a drive motor 6 by way of a plurality of supports 47. A fan 5 is secured to the output shaft 6a of the drive motor 6 by using a nut 50 in order to cause centrifugal air flow, and situated in the second duct 32b (second air path 3b). There are provided a plurality of outlets 2 (4 outlets in the present embodiment) at adequate intervals in the second duct 32b. Connectors (not shown), which form bases of nozzles 2a and are curved at proper angles (for example, 90 deg.), are rotatably connected to the outlets 2.

As shown in FIG. 8, the bases of arms 51 made of hollow casings are rotably provided at portions where each of the outlets 2 of the body 31 is situated. In the arm 51, the a nozzle 2a and a venturi tube 11 facing the same are situated. Furthermore, there is formed a secondary air inlet slit 52 in the arm 51 at a portion where the nozzle 2a faces toward the nozzle 11. Arms 51 are provided so that they are oriented differently from each other (at 90 deg. in the present embodiment) in terms of rotational surface including rotational locus.

In addition, the present embodiment is equipped with 4 arms 51, but they should not always be in such a quantity. If 5 arms 51 are provided, it is possible to orient them at an angular of 72 deg. different from each other. If 6 arms 51 are provided, an angular difference of 60 deg. may be applicable.

There are secured a plurality of supporting members 53 to a ceiling 19 by using screws 55. Each of the supporting members 55 has a hole (not shown) and a long hole 53a connected thereto. An engaging member 56 with an engaging element 56a at the tip is secured on the body 31. The air circulator $U_5$ is attached removably to the ceiling 19 by engaging the engaging element 56a with the long hole 53a of the supporting member 53.

The air circulator $U_5$ is thus composed, and when a controller 20 (as shown in FIG. 4) is so operated as to rotate the motor 6 and the fan 5, most of the air in the interior to be sucked passes an air filter 37, reaching the first duct 32a, and the rest in a small quantity is sucked into the cartridge 39 via the vent hole 40 before it is sucked into the air path 3a through the vent hole 41 by way of the air path.

The primary air thus suck is cleaned when passing the air filter 37 while the air passing the cartridge 39 is scented by the aromatic 7 contained in the cartridge 39 and mixed well by air supplied by the fan 5 before it is discharged into the inlet of the venturi tube 11 through the nozzle 2a at an outlet 2. When mixed air is discharged into the venturi tube 11, the secondary air in the surrounding is sucked thereinto through the secondary air suction slit 52 and discharged indoors through the venturi tube outlet 11. The air thus discharged can be controlled for direction by adjusting each of the arms 51 angularly against the ceiling 19 to arrange them radially. The top air in the interior containing fragrance is evenly supplied downward to four corners and peripherally, eliminating any pool of hot and cold air in an efficient manner. By adjusting inclination angles of the arm 51, it may satisfy any condition of an interior space of a different shape or size and a large installation in terms of air control.

When the secondary air is discharged, most of the primary air sucked in the air circulator $U_5$ passes the air filter 37 and the rest passes the cartridge 39, preventing the aromatic 9 in the cartridge from consuming soon despite that a lot of air is sucked in the air path 3. In addition, if the deodorant 7 is put in the cartridge 39 instead of the aromatic 9, it will help the air filter 37 to dissipate such a smell as common to a hospital, a restaurant or a ship and to clean the air while eliminating any pool of hot and cold air.

When either of the aromatic 9 and the deodorant 7 is put in the cassette 36, and is reduced in fragrance emitting or in deodorizing, the cassette 36 itself can be removed from the body 31 to renew the aromatic 9 or the deodorant 7 and the air filter 37. If there is a lot of cassettes 36, each having a cartridge 39 containing an aromatic 9 or a deodorant 7 and an air filter 37, the cassette 36 can be renewed with a new cassette 36.

As described above, the cartridge 39 according to the present embodiment contains either an aromatic 9 or a deodorant 7. It is possible, however, to use a cassette to contain a deodorant as well as an aromatic, and FIG. 11 gives an illustration of such a cartridge.

Figure 11:
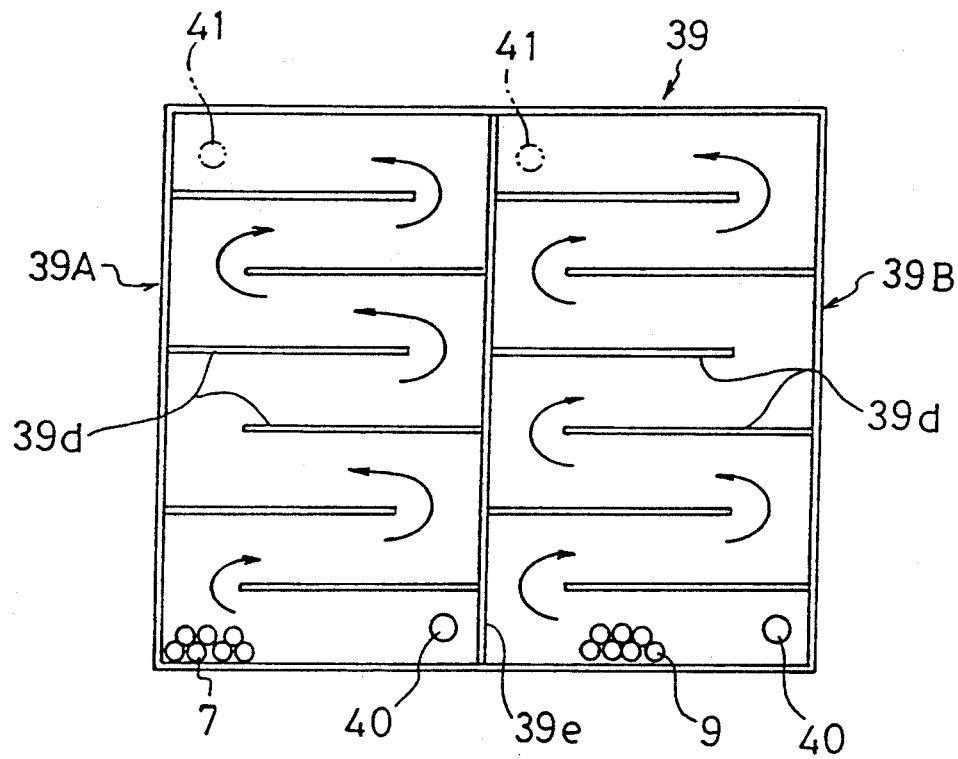
FIG. 11 is a plan view of a modified cartridge.

FIG. 11 is a plan view of the cartridge which is able to contain both a deodorant 7 and an aromatic 9. As shown in the figure, the cartridge 39 (container) is divided into a cartridge 39A to accommodate a deodorant 7 and a cartridge 39B to contain an aromatic by a separator 39e. Each of the cartridges 39A and 39B is provided with a partition 39d and vent holes 40, 41. The deodorant containing cartridge 39A deodorizes the air passing therein so that it may deodorize the air in the interior while the aromatic containing cartridge 39B gives out a fragrance to the air passing therein to enable it to scent the air in the interior.

Figure 12:
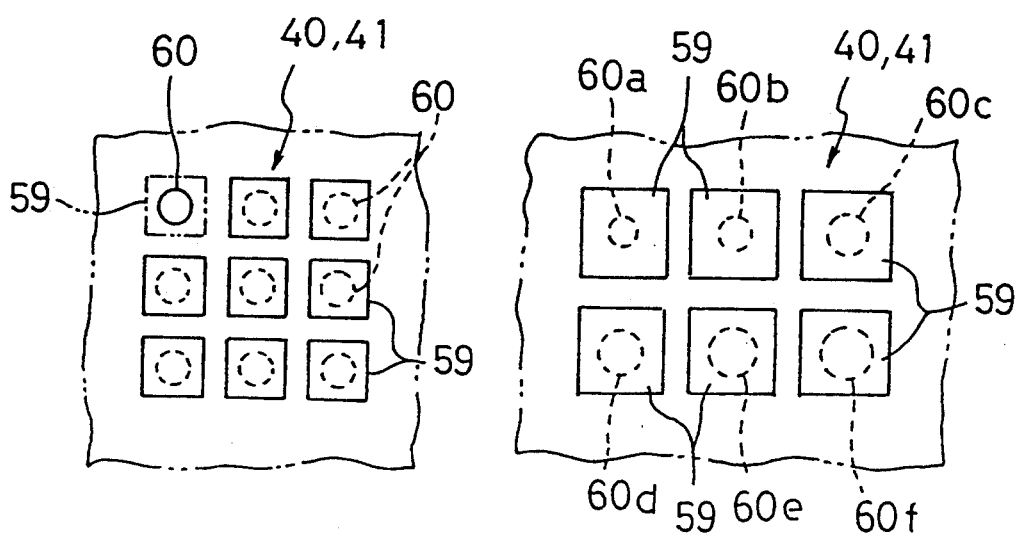
FIGS. 12(a) and 12(b) are plan views of cartridges having modified vent holes respectively.

In the embodiment described referring to FIG. 8 through FIG. 10, the amount of air passing in the cartridge 3, when the primary air is sucked into the air circulator $U_5$, is fixed to a certain level due to the dimensions of the vent holes 40, 41 (refer to FIG. 10) provided in the cartridge 39. According to the construction of the embodiment, it is not possible to control the odor emitting ratio of the aromatic 9 (or the deodorizing rate of the deodorant 7) unless the suction amount of the primary air increases or decreases. FIG. 12 shows modified vent holes 40, 41 so as to allow the deodorant ratio or odor emitting ratio to be controlled as desired.

As shown in FIG. 12(a), the vent hole 40 (or the vent hole 41) in the cartridge 39 is composed of vent holes 60 having a plurality of holes with the same diameter, and each of the vent holes 60 is closed with a removable sticker 59 when not in use. In order for the air circulator $U_5$ to be used, it is necessary to remove from vent holes 60 stickers 59 in a given quantity to provide an opening as desired, enabling thereby the odor emitting ratio or deodorizing rate of air that passes the cartridge 39 to be controlled as desired by the user.

FIG. 12(b) gives an illustration of another modification of a vent hole 40 (or a vent hole 41). In the figure, the vent hole 40 is composed of a plurality of vent holes 60a–60f different in radius. They are closed with stickers 59 as in the case of the vent hole 60. When using the air circulator $U_5$, it is necessary to select a single vent hole or a desired combination of a plurality of vent holes 60a–60f and remove accordingly (a) sticker(s) 59 to provide the desired opening area of the vent hole 40 (or vent hole 41), thereby setting the odor emitting or the deodorizing rate at a desired level.

Figure 13:
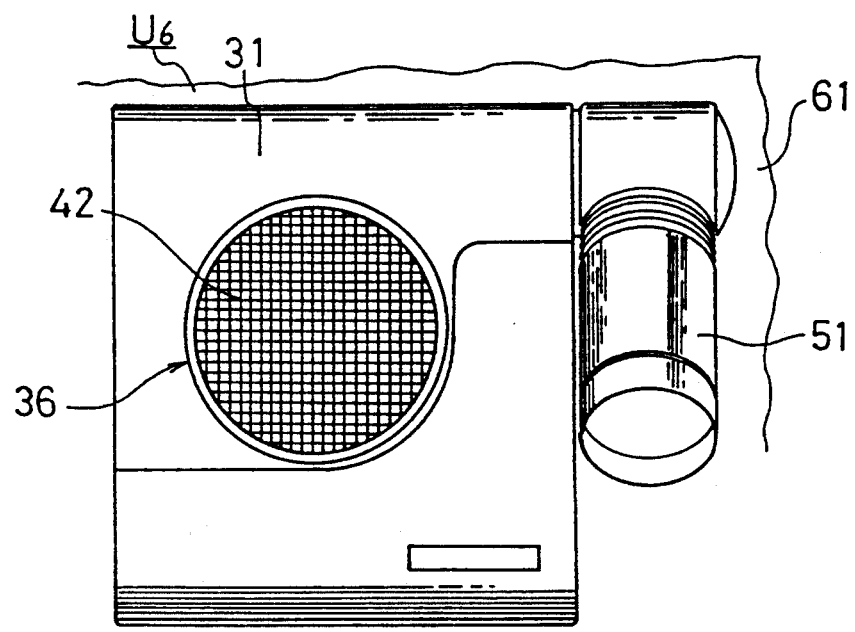
FIG. 13 is an elevation view of an air circulator of another modified embodiment of the present invention.
Figure 14:
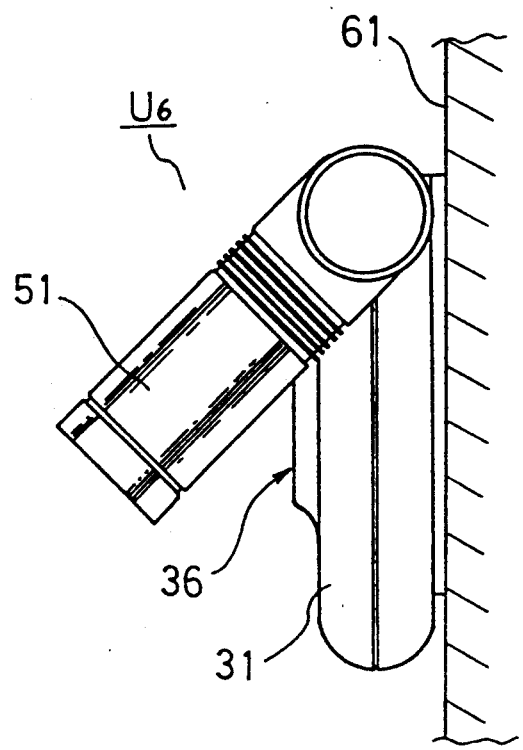
FIG. 14 is a side view thereof.

FIG. 13 and FIG. 14 show an partially modified air circulator embodied according to the present invention. As shown in them, the body 31 of an air circulator $U_6$ is provided with an (discharge) arm 51 free to incline as in the previous embodiment. The body 31 is removably engaged with an engaging member (not shown) on the wall 61. The wall-mount air circulator $U_6$ is suitably installed in a comparatively small interior. In the present embodiment, there is used a single arm 51, but the body 31 can be provided with a plurality of arms 51 so that their inclination angles may be adjusted for inclination to give out fragrance to and clean the primary air in the interior while dissipating any pool of hot and cold air.

Figure 15:
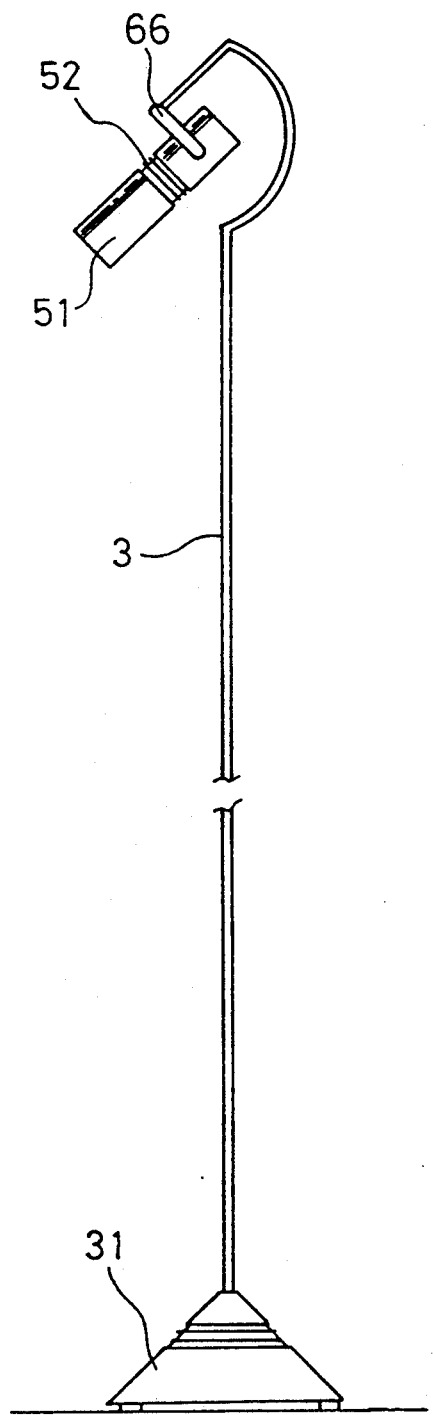
FIG. 15 is a side view of another air circulator of an embodiment according to the present invention.
Figure 16:
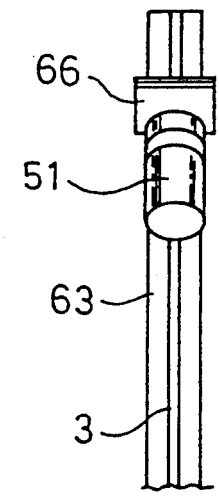
FIG. 16 is an elevation view showing the main parts thereof.
Figure 17:
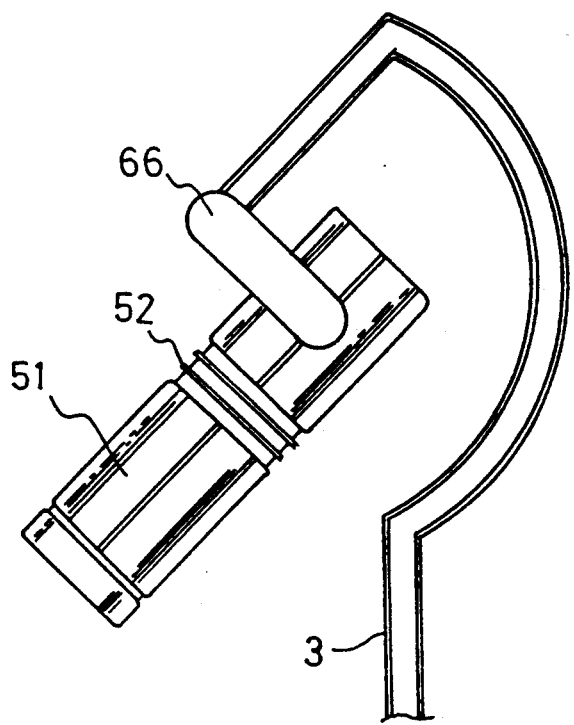
FIG. 17 is a side view showing the arm thereof.

FIG. 15 through FIG. 17 give an illustration of another partially modified air circulator according to the present invention.

As shown in them, the air circulator $U_7$ is of a stand type, and the support is the body 31 of the air circulator $U_7$. There are provided in the body a cassette 36 containing an air filter 37 and a cartridge 36 (see FIG. 9), and similar items as a drive motor 6 and a fan (not shown). An air path 3 composed of a hollow support and having a rib 63 on both sides stands on the body 31, and there is secured a supporting member 66 to the front end of the air path 3, and the arm 51 is inclinably mounted onto the supporting member 66.

The air circulator $U_7$ is put into operation when the switch (not shown) is handled, enabling the body 31 to suck the primary air, which passes the air path 3 and support member 66 to reach the arm 51. The air is discharged downward into the interior through the arm discharge port while sucking the secondary air in the surrounding through the arm secondary air slit 52. The air circulator $U_7$ herein has a single arm 51, but a plurality of arms 51 may be mounted onto the air path 3. The air circulator $U_7$ can also be equipped with an illumination apparatus so that it can be used as a lighting stand as well. Since the air circulator $U_7$ needs a rather small installation space and is easy to move, it can suitably be brought into and used in any narrow interior as necessary where deodorizing, emitting fragrance and air cleaning are required.

The cartridge (container) 39 in the cassette 36 can also contain a hygroscopic agent, repellent or anti-rust agent in addition to a deodorant 7 and an aromatic 9 to be used for damp-proofing and repelling in a shed, a closet, a warehouse or a library where the air circulator $U_7$ is installed.

As seen from above, there is provided a container (10 or 39) interposed in the air path (3) of every air circulator according to the present invention, and each circulator simple in construction may be readily installed in an interior space to deodorize, giving out fragrance to and circulate the air so that a comfortable and cozy atmosphere can be produced. In addition, each circulator is also able to supply a hotel with any fragrance unique thereto for identification or distinction by odor.

Since there is provided a venturi tube to face the outlet (2) of a blower (5), the venturi tube sucks the surrounding air due to the air coming from the outlet (2), enhancing the efficiency of indoor air circulation. This makes it possible, in addition, to depend on a blower (5) and a drive motor (6) of a smaller capacity but with a higher efficiency, which in turn serves to keep the interior quiet because of reduced motor and air noises.

Furthermore, the circulation of air in the interior (A) is made when the air comes out of the outlet (2) and the air sucked by the venturi tube (11) is discharged as well. As a result, only part of the circulating air passes the deodorant (7) or the aromatic (9) contained in the container (10). This enables the effects of deodorizing and scenting by the deodorant (7) and aromatic (9) to equilibrate with the air circulation effects by heating or cooling. This also helps prevent a deodorant or an aromatic from being deteriorated at an earlier stage, providing a simpler maintenance of such agents.

When a filter is supplied at the inlet together with an air treating agent containing container (39), the air in the interior can be not only deodorized and given a fragrance but also cleaned.

If the venturi tube (11) or the arm (51) is made adjust an angle or inclination, the air can be ejected evenly toward the corners and peripheries by the air circulator ($U_5$), eliminating any pool of hot and cold air in an effective manner. In particular, if a plurality of arms 51 composed of outlets (2) and venturi tubes (11) are provided around the body 31, a better air circulation efficiency will be feasible.

Since a container (39) and a filter (37) are contained together in a cassette (36) and the cassette (36) can be attached removably to the body (31), the renewal of air treating agents such as a deodorant and an aromatic, and filters can be carried out more readily.

What is claimed is:

1. An air circulator comprising,
   a body including an inlet adapted to open to an interior space, an outlet adapted to open to the interior space and an air path for connecting between the inlet and the outlet,
   a blower situated in the air path and having a motor for driving the blower,
   a container connected to the inlet, said container containing at least an air treatment agent therein, and
   a venturi tube attached to the outlet and having means to suck surrounding air, said venturi tube discharging the surrounding air and the air inhaled through the inlet and the container and ejected from the outlet by means of the blower.

2. An air circulator as claimed in claim 1, wherein the venturi tube is inclinably connected with the outlet.

3. An air circulator as claimed in claim 1, wherein the container is removably mounted onto the inlet.

4. An air circulator as claimed in claim 1, further comprising a filter in the air path parallel to the container in order to filter the air.

5. An air circulator as claimed in claim 4, further comprising a cassette containing the filter and the container therein, said cassette being removably attached to the inlet.

6. An air circulator as claimed in claim 5, wherein said container is situated in the center of the cassette and the filter is situated around the container.

7. An air circulator as claimed in claim 5, wherein said container has an inlet hole at one side, an outlet hole at another side, and a plurality of partitions to provide an air path in the container extending from the inlet hole to the outlet hole.

8. An air circulator as claimed in claim 5, wherein said container has a separator to divide into a plurality of portions, different air treatment agents being retained in the portions.

9. An air circulator as claimed in claim 5, wherein said container has a plurality of inlet holes, outlet holes, and stickers for closing the inlet and outlet holes, said stickers being removed from the container in use.

10. An air circulator as claimed in claim 1, wherein the air treatment agent is a deodorant.

11. An air circulator as claimed in claim 1, wherein the air treatment agent is an aromatic.

12. An air circulator as claimed in claim 1, wherein the air treatment agent is a combination of a deodorant and an aromatic.

13. An air circulator as claimed in claim 1, wherein said air path is forked to form forked paths, each forked path having an inlet, said air circulator having a plurality of containers attached to the respective inlets, each container containing the air treatment agent and having a shutter to shut off the air passing through the container.

14. An air circulator as claimed in claim 13, wherein said containers attached to the inlets of the forked paths have the air treatment agents different from each other.

15. An air circulator as claimed in claim 1, further comprising a lighting apparatus, said body being installed in the lighting apparatus.

16. An air circulator as claimed in claim 1, further comprising an arm connected to the body, said outlet and the venturi tube being located inside the arm.

17. An air circulator as claimed in claim 16, further comprising a stand for constituting a support, said air path being arranged in the stand, and the arm being inclinably arranged at a top of the support.

18. An air circulator as claimed in claim 16, wherein a plurality of arms are disposed around the body.

19. An air circulator as claimed in claim 16, wherein the arm is inclinably connected to the body.

* * * * *